(12) United States Patent
Matsuda et al.

(10) Patent No.: US 8,079,473 B2
(45) Date of Patent: Dec. 20, 2011

(54) MEDICAL DEVICE HOLDER, METHOD OF RETRIEVING MEDICAL DEVICE, AND A PACKAGED MEDICAL DEVICE

(75) Inventors: Junko Matsuda, Shizuoka (JP); Hiroshi Yagi, Shizuoka (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 9 days.

(21) Appl. No.: 12/510,644

(22) Filed: Jul. 28, 2009

(65) Prior Publication Data

US 2010/0025273 A1    Feb. 4, 2010

(30) Foreign Application Priority Data

Jul. 30, 2008  (JP) .................................. 2008-197011

(51) Int. Cl.
*A61B 17/06* (2006.01)
(52) U.S. Cl. ......... 206/438; 206/363; 206/364; 206/571
(58) Field of Classification Search .................. 206/370, 206/363, 438, 571, 214, 495, 364
See application file for complete search history.

(56) References Cited

U.S. PATENT DOCUMENTS

| 2004/0243214 A1* | 12/2004 | Farrell et al. ................. 623/1.11 |
| 2005/0033430 A1* | 2/2005 | Powers et al. .............. 623/17.11 |
| 2007/0244500 A1* | 10/2007 | Lucas et al. ................... 606/194 |

FOREIGN PATENT DOCUMENTS

JP      2000-255627      9/2000

* cited by examiner

*Primary Examiner* — J. Gregory Pickett
*Assistant Examiner* — Raven Collins
(74) *Attorney, Agent, or Firm* — Buchanan Ingersoll & Rooney PC

(57) ABSTRACT

A medical device holder is comprised of a flexible elongated sheet member, and includes a holding portion configured to hold a three-dimensionally configured part connected of the device. The holding portion is configured to bend back on itself to cover the three-dimensionally configured part. A slit is provided in the sheet member to allow insertion of the distal end portion of the holding portion so that the state in which the holding portion covers the three-dimensionally configured part connected can be maintained. The distal end portion of the holding portion is folded toward the opposite direction from the direction to pull out when retrieving the catheter from the sheet member.

19 Claims, 12 Drawing Sheets

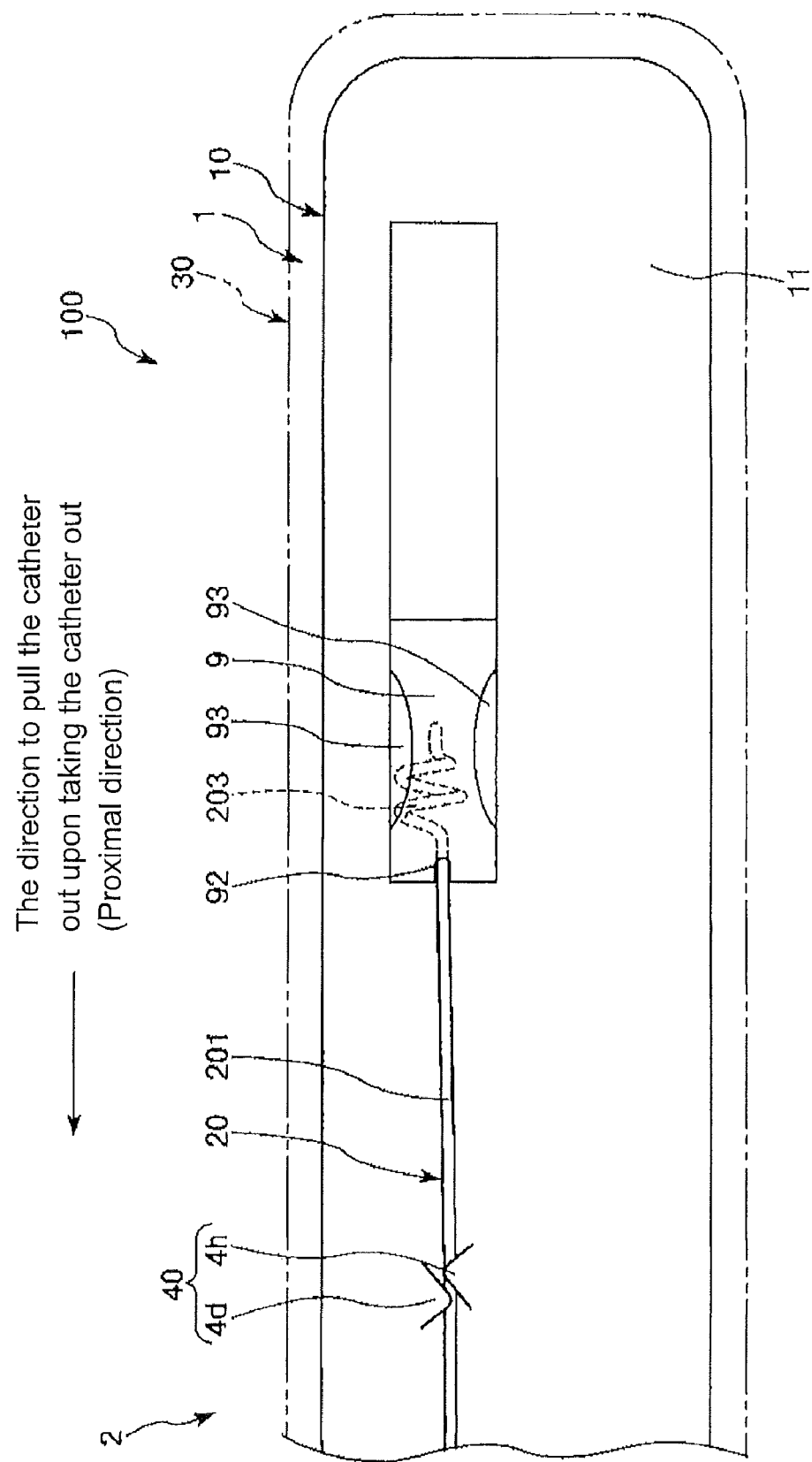

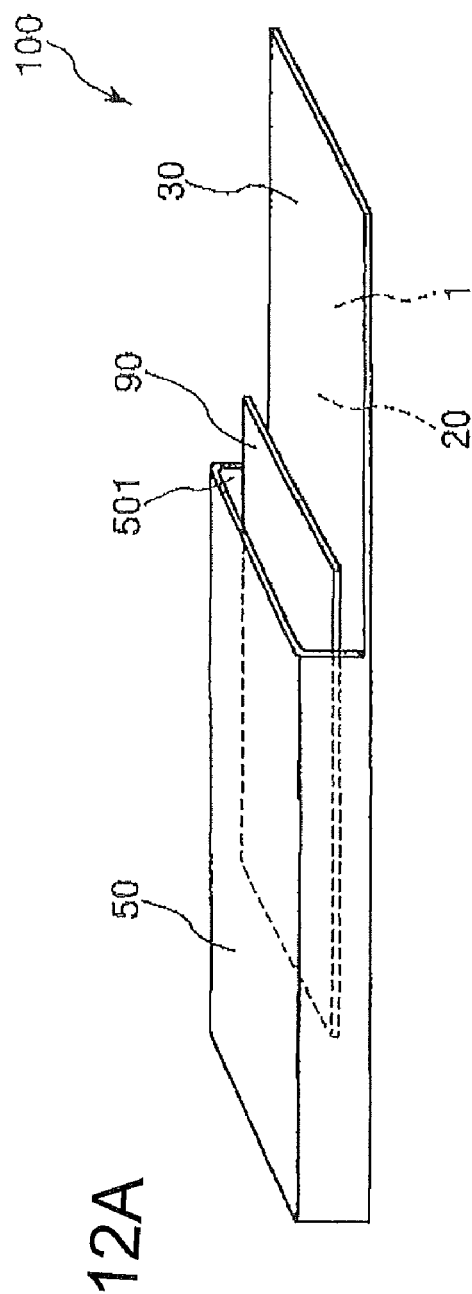
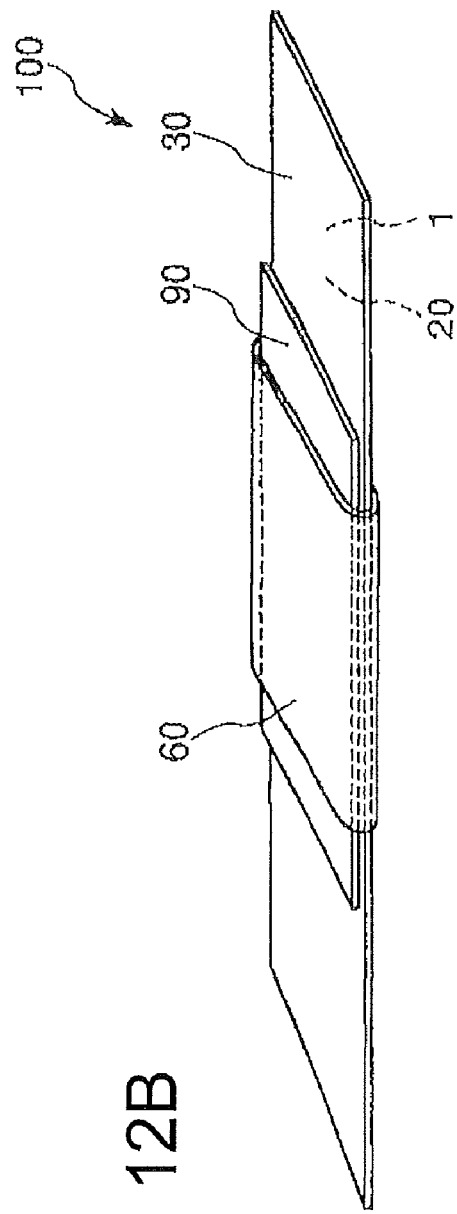
Fig. 12A
Fig. 12B

MEDICAL DEVICE HOLDER, METHOD OF RETRIEVING MEDICAL DEVICE, AND A PACKAGED MEDICAL DEVICE

TECHNOLOGICAL FIELD

The disclosure here relates to a medical device holder, a method of retrieving a medical device, and a packaged medical device.

BACKGROUND DISCUSSION

Japanese Application Publication No. 2000-255627 discloses a flexible elongated medical device such as a catheter fixedly held on a card, and packaged (stored) in a bag-shaped packaging member in an unused state.

The card described in Japanese Application Publication No. 2000-255627 is formed of a flexible elongated sheet member. This card is formed with a plurality of flexible fixing belts and a plurality of groove holes for allowing insertion of distal end portions of the fixing belts arranged in parallel along the longitudinal direction of the catheter. The fixing belts each wrap around the catheter in the direction vertical to the longitudinal direction of the catheter (sheet member) and are inserted into the corresponding groove holes, whereby the catheter is held.

The card disclosed in Japanese Application Publication No. 2000-255627 may not be well suited to holding, and allowing storage in a packaging member, a medical device having a bulk connecting member (a structure having a three-dimensional structure) such as a three-way stopcock at a distal end portion of a tube connected to a hub provided at a proximal end portion of the catheter.

First of all, since the catheter is held on the card in a state in which the three-way stopcock is exposed, the packaging member might become damaged by the three-way stopcock, and also the three-way stopcock might be displaced or wobble.

Since a plurality of the packaged catheters are sometimes stored in one box together, the three-way stopcock might be caught by other three-way stopcocks or some other members of adjacent catheters when retrieving the packaged catheter from the box, so that it cannot be retrieved easily or the packaging member might become damaged.

SUMMARY

According to one aspect, a packaged medical device includes a medical device and an elongated sheet member sealed within a package. The medical device comprises a flexible linear portion and a three-dimensionally configured part, with the distal end portion of the flexible linear portion connected to the three-dimensionally configured part, and the three-dimensionally configured part being enlarged relative to the distal end portion of the flexible linear portion. The medical device is held on the elongated sheet member, and the sheet member possesses a proximal end and a distal end. The sheet member comprises a slit passing through the sheet member and a holding portion possessing a distal end portion. A first part of the holding portion underlies the three-dimensionally configured part and a second part of the holding portion overlies the three-dimensionally configured part so that the three-dimensionally configured part is covered by the holding portion. The distal end portion of the holding portion extends through the slit in the sheet member and is folded back toward the distal end of the sheet member in a direction opposite a direction in which the medical device is pulled to remove the medical device from the holder.

According to another aspect, a medical device holder is configured to hold a medical device provided with a three-dimensionally configured part at an end portion of a flexible linear portion. The medical device holder includes an elongated sheet member for holding the medical device and to permit the medical device to be separated from the sheet member by applying a force to the medical device moving the medical device in a proximal direction relative to the sheet member. The sheet member is comprised of a holding portion and an insertion portion. The holding portion is an elongated part of the sheet member outlined by an incision which separates the elongated part from a surrounding part of the sheet member to allow the holding portion to be moved relative to the surrounding part of the sheet member and be bent back upon itself to cover and hold the three-dimensionally configured part of the medical device. The insertion portion of the holding portion comprises a slit passing completely through the sheet member for receiving the distal end portion of the holding portion after the holding portion is bent back upon itself in a longitudinal direction of the holding portion to cover the three-dimensionally configured part of the medical device. The distal end portion of the holding portion is adapted to be folded back in a distal direction opposite the proximal direction after the distal portion is inserted into the slit.

Another aspect pertains to a method of retrieving a medical device from a medical device holder. The medical device holder includes an elongated sheet member possessing a distal end, and packaging in which the medical device and the sheet member are sealed. The medical device comprises a flexible linear portion and a three-dimensionally configured part connected to a distal end portion of the flexible linear portion. The sheet member comprises a slit passing through the sheet member and a holding portion possessing a distal end portion, with the three-dimensionally configured part being positioned on the sheet member while the holding portion covers the three-dimensionally configured part. The distal end portion of the holding portion extends through the slit in the sheet member and is folded back in the distal direction toward the distal end of the sheet member. The method involves opening the packaging to gain access to the sheet member and the medical device, and pulling the medical device in a proximal direction, opposite the direction in which the holding portion is folded back, to move the medical device relative to the sheet member and cause the three-dimensionally configured part to apply a force to the holding portion which pulls the distal end portion of the holding portion out of the slit so that the medical device is separable from the sheet member.

Preferably, the holding portion envelopes the structure substantially entirely, and the distal end portion of the holding portion is configured to allow insertion of the linear portion. In addition, the distal end portion of the holding portion is preferably formed with a hole which allows insertion of the linear portion and is opened at a distal end of the distal end portion of the holding portion.

The holding portion preferably includes an opening on the proximal end side thereof. The holding portion is preferably formed by incising part of the sheet member, and preferably includes wall portions formed by folding longitudinal edge portions in the widthwise direction. The holding portion can be provided at a midsection of the sheet member.

The holding portion can be provided at an end portion of the sheet member in the longitudinal direction. The inserted portion is formed by incising part of the sheet member. The sheet member can be formed with a resin layer formed of a resin material on at least a front surface thereof. Preferably, the thickness of the sheet member is from 0.20 to 0.55 mm. The holding portion has an elongated rectangular shape.

According to the embodiments disclosed here, the structure provided at the end portion of the flexible linear portion of the medical device is held reliably. In addition, since the holding portion covers the structure, the packaging member is inhibited from becoming damaged (broken) by the structure when the medical device is stored in the bag-shaped packaging member in a state of being held by the medical device holder, whereby the medical device is held adequately, and the medical device is transported and stored in an adequate state.

Since the distal end portion of the holding portion is folded back toward the opposite side from the direction to pull out when retrieving the medical device from the medical device holder (is pulled out in the direction opposite from the direction in which the distal end portion of the holding portion is folded back when retrieving the medical device from the medical device holder), when retrieving the medical device held on the medical device holder. That is, with the medical device held on the medical device holder and stored in the packaging member, the distal end portion of the holding portion is inhibited or prevented from being caught by the packaging member, whereby the distal end portion of the holding portion comes out from the inserted portion smoothly and reliably, so that the retrieving operation thereof is achieved quite easily and quickly.

Since the holding portion is folded along the direction to pull out when retrieving the medical device from the medical device holder and covers the medical device (since the holding portion covers the structure by being folded along the longitudinal direction of the medical device holder), the side surface near an apex of the holding portion (a portion of the holding portion located at a highest level from the medical device holder when covering the structure) is prevented from being caught by an inner surface of the packaging member when retrieving the medical device and the medical device holder stored in the packaging member from the packaging member.

Also, when retrieving a plurality of the medical devices stored in a storage container in a state of each being held on the medical device holder, that is being held on the medical device holder and stored in the packaging member from the storage container together with the packaging member, the structure is prevented from being caught by structures of other adjacent medical devices or a certain member thereof by the holding portion, so that the retrieving operation is achieved relatively easily and quickly.

BRIEF DESCRIPTION OF THE DRAWING FIGURES

FIG. 11 is a plan view of a principle portion of the medical device holder shown in FIG. 10 in the state of usage.

FIG. 12A is a perspective view of another configuration example of a medical device set having the medical device holder disclosed here.

FIG. 12B is a perspective view schematically showing another configuration example of a medical device set having the medical device holder disclosed here.

DETAILED DESCRIPTION

Figure 1:
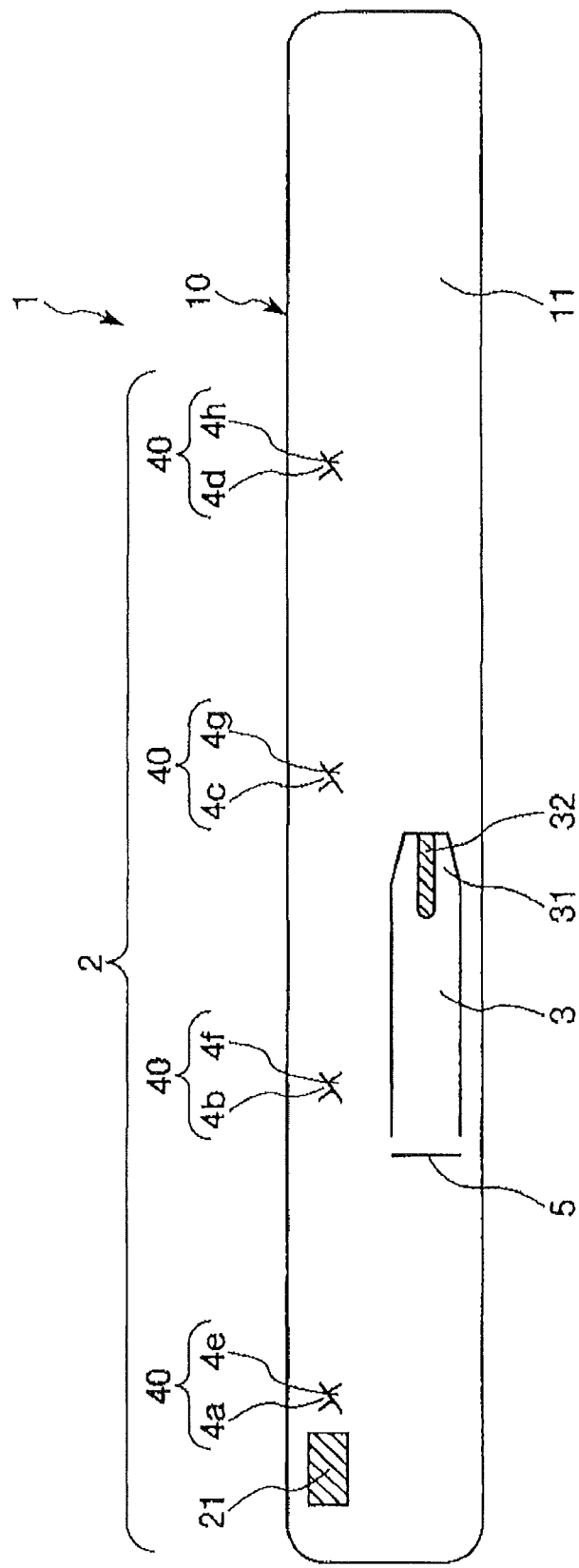
FIG. 1 is a plan view of a medical device holder according to a first embodiment disclosed here.
Figure 2:
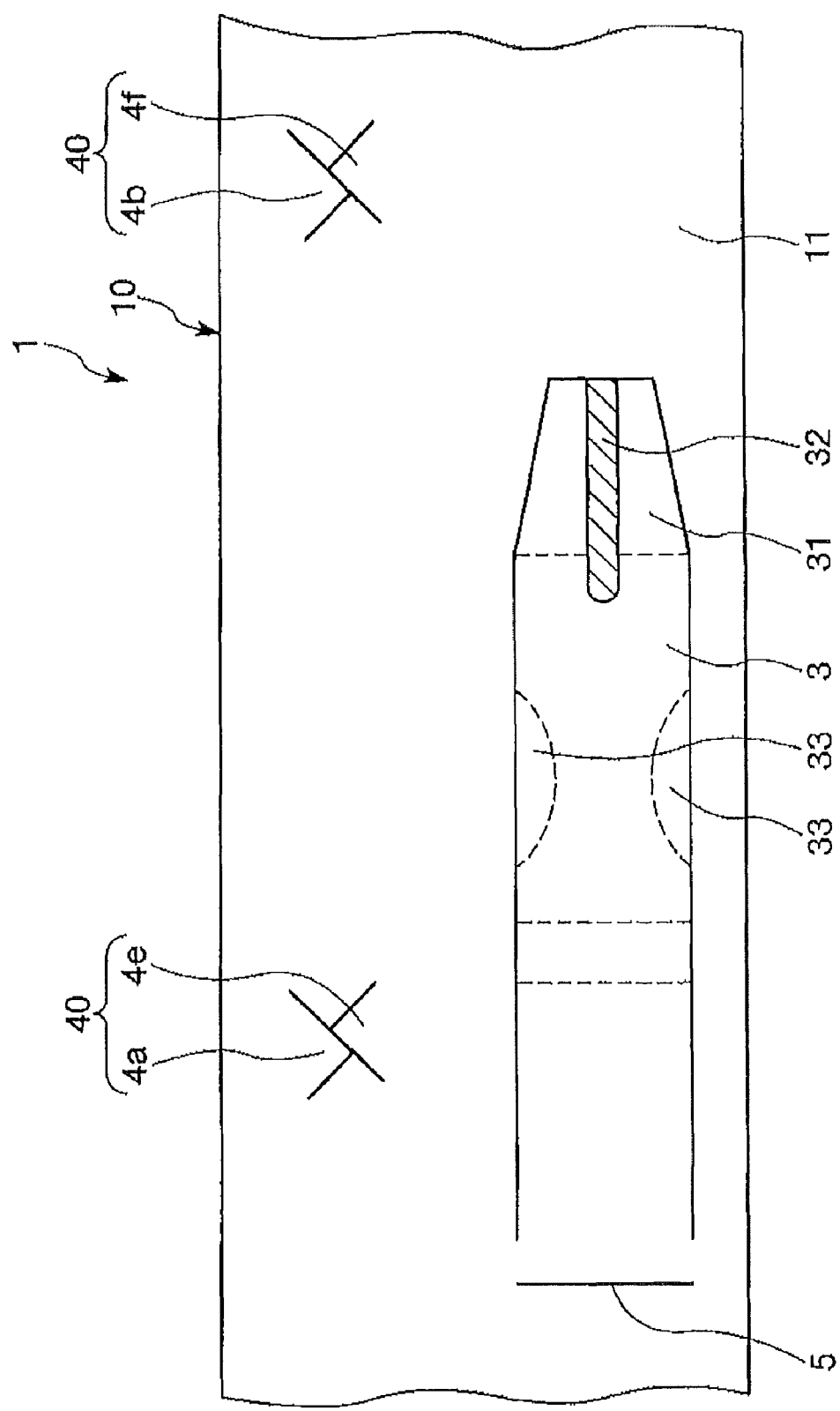
FIG. 2 is a plan view of a portion of the medical device holder shown in FIG. 1 in the vicinity of a holding portion.
Figure 3:
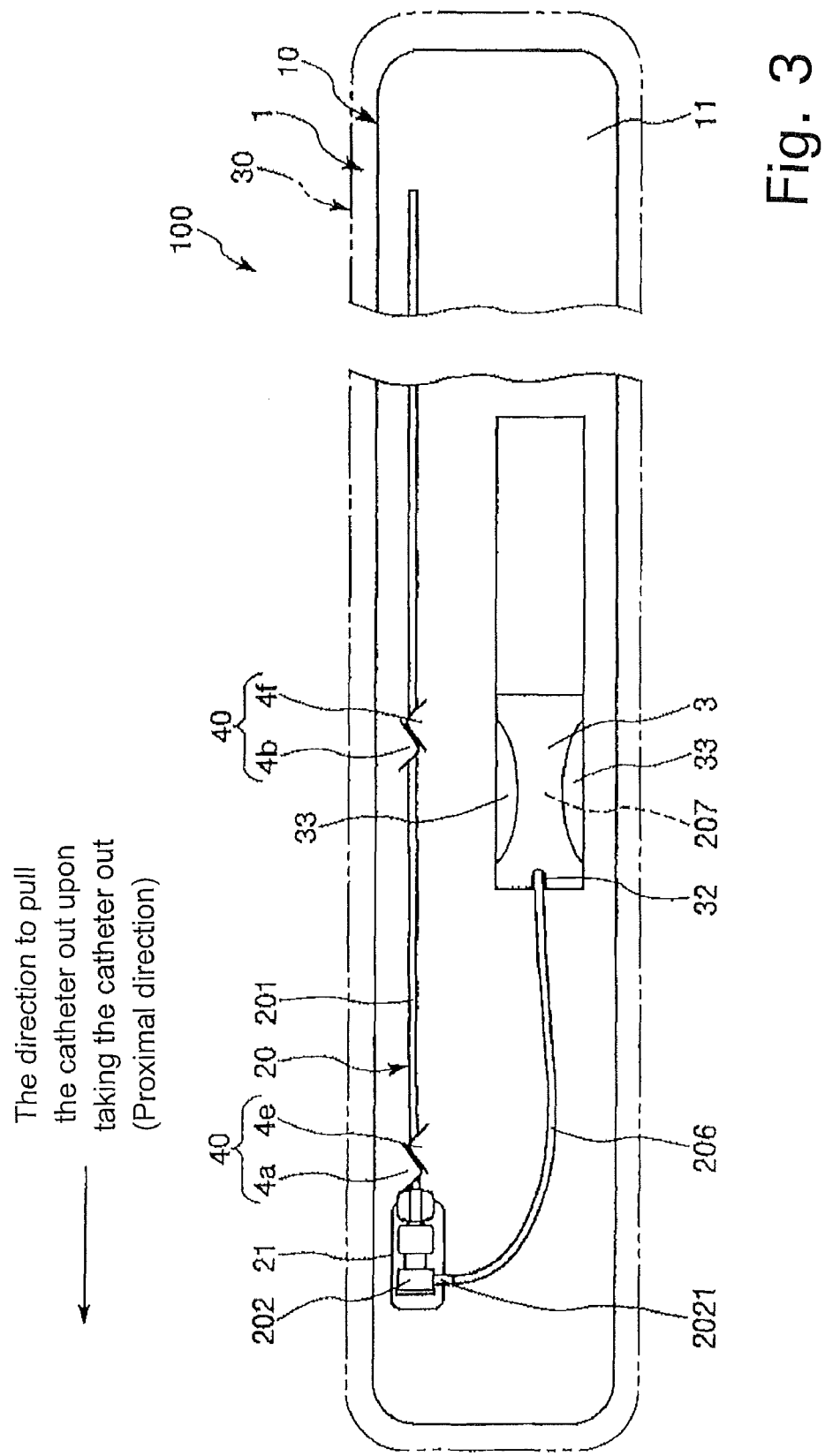
FIG. 3 is a plan view illustrating the medical device holder shown in FIG. 1 in a state of usage.
Figure 4:
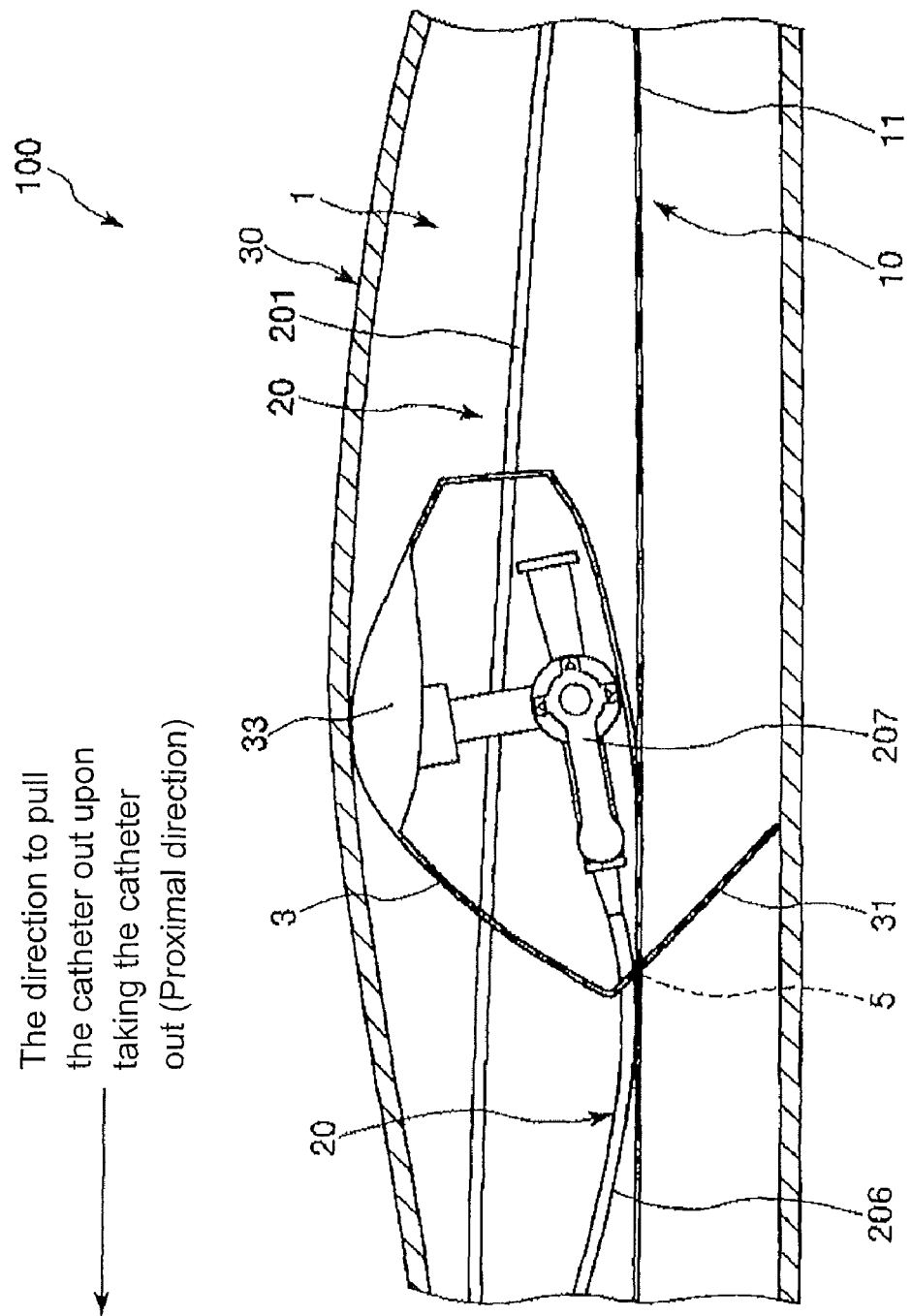
FIG. 4 is a side view showing a portion of the medical device holder shown in FIG. 1 in the vicinity of the holding portion in the state of usage.

A medical device holder, a method of retrieving a medical device, and a packaged medical device according to the disclosure here are described in detail on the basis of preferred embodiments shown In the following description, the right side or right end in FIGS. 1-4 are referred to as the "distal end", and the left sides or left ends are referred to as the "proximal end". The near (front) sides of the sheets in FIGS. 1-3 are referred to as the "front", the far (back) sides of the sheets are referred to as the "back", the upper sides in FIG. 4 are referred to as the "front", and the lower sides are referred to as the "back".

Broken lines in FIG. 2 indicate portions to be valley folding portions and solid lines indicate incised portions (i.e., portions which, in the disclosed embodiment, are cut completely through the sheet member so that the portions of the sheet member on either side of the incised portion are separated from one another by the incised portion). Hatched portions in FIG. 1 and FIG. 2 indicate through holes (openings).

This embodiment of the medical device holder is a sheet-shaped or sheet-made medical device holder. The sheet-shaped or sheet-made medical device holder (hereinafter referred to simply as a holder or medical device holder) 1 shown in FIGS. 1-4 is able to hold an unused medical device 20. In the illustrated embodiment, the medical device is a catheter. Hereinafter, the state in which the medical device holder 1 holds the catheter 20 is referred to as the "holding state". The medical device holder 1 is stored in a packaging member (e.g., bag or package) 30 together with the catheter 20 in this holding state (see FIG. 3). The packaging member in the state shown in FIG. 3 is referred to as a "catheter set (medical device set) 100".

Before describing the medical device holder 1, the catheter 20 and the packaging member 30 will be described, beginning with a description of the catheter 20.

As shown in FIG. 3 and FIG. 4, the catheter 20 includes a flexible catheter body (linear portion or elongated portion) 201, a hub 202 at the proximal end portion of the catheter body 201, a flexible tube (linear portion) 206 connected to the proximal end side of the catheter body 201, that is to the hub 202, and a three-way stopcock (connecting member or structure having a three-dimensional configuration) 207 provided at a distal end portion of the tube 206. The three-way stopcock 207 is an example of a three-dimensionally configured part of a medical device which is enlarged relative to the adjoining distal end portion of the flexible linear portion 206.

The catheter body 201 is in the form of an elongated tube (hollow tube).

The hub 202 formed of a hard resin material is fixed (connected) to the proximal end portion of the catheter body 201. The hub 202 is in the form of a cylindrical member having an outer diameter and an inner diameter larger than the outer diameter and the inner diameter respectively of the catheter body 201, and a bore of the hub is communicated with a bore of the catheter body 201. The side portion of the hub 202 is provided with a port portion 2021 having a bore in communication with the bore of the hub.

A proximal end portion (one of the ends in the longitudinal direction) of the flexible elongated tube (hollow tube) 206 is fixed (connected) to the port portion 2021 of the hub 202 so that the tube 206 interior is communicated with the bore of the hub. Then, the three-way stopcock 207 formed of a hard resin material is fixed (connected) to the distal end portion (the other end portion in the longitudinal direction) of the tube 206 as a connecting member (structure having a three-dimensional configuration) which allows detachable attachment of a predetermined member (medical device) so as to communicate with a bore of the tube 206.

In the configuration shown in the drawing figure, the proximal end portion of the tube 206 is fixed to the hub 202. However, the disclosure here is not limited to this, and may be detachably connected to the hub 202, for example.

The connecting member is not limited to the three-way stopcock as long as it is a device (means) which allows connection of the predetermined member, and may be branch connectors such as a Y-shaped tube, a T-shaped tube, or a y-shaped tube and hubs as other means.

The material forming the catheter body 201 is not specifically limited. By way of example, the material may be various types of thermoplastic elastomer such as styrene-based, polyolefin-based, polyurethane-based, polyester-based, polyamide-based, polybutadiene-based, trans-polyisoprene-based, fluorine-contained rubber-based, chlorinated polyethylene-based, and one or a combination of two or more of those (polymer alloy, polymer blend, laminated member, etc.) may be used.

The packaging member, package or enclosure 30 is now described. As shown in FIG. 3 and FIG. 4, the packaging member 30 possesses an elongated shape (elongated bag shape), and has a size sufficient to store the entire medical device holder 1 in the holding state. The packaging member 30 is formed into a bag shape by superimposing flexible sheets (sheet members) formed of a soft resin such as polyethylene or polyvinyl chloride and fusion bonding together (thermal fusion bonding, high frequency fusion bonding), or adhesive bonding together, the peripheral edges of the sheets other than the proximal end portion of the sheets. One of both sides of the packaging member 30 may be formed of paper material, woven cloth, or nonwoven cloth.

A distal end portion (one of the ends in the longitudinal direction) is not fusion bonded or otherwise bonded together, but is formed as an opening until the medical device holder 1 in the holding state is inserted into the packaging member 30. In this way, the distal end portion of the package or enclosure 30 is used as an insertion port for inserting the medical device holder 1 in the holding state into the packaging member 30. Once the medical device holder 1 is inserted into the package 30, the open end of the package is fusion bonded or otherwise bonded to effect sealing after insertion of the medical device holder 1 into the packaging member 30 so that the medical device and the holder are sealed inside the package 30. The proximal end portion (the other end portion in the longitudinal direction) is used as an output port when retrieving the catheter 20 from the medical device holder 1 stored in the packaging member 30 by forming an opening by separating the fusion bonded or bonded portion. The medical device inside the package is sterilized. This can be accomplished by sterilizing the package with Ethylene oxide gas (EOG) and using a package which permits the EOG to permeate into the package.

Preferably, at least a front side of the packaging member 30 is substantially transparent to permit visibility to the interior of the packaging member 30. For example, the packaging member 30 may be formed (configured) of a substantially transparent resin sheet on one surface (front side) of the packaging member 30 and of a gas-permeable nonwoven cloth (for example, TYVEK (registered trademark)) and the like on the other surface (back side) of the packaging member 30 for sterilization with ethylene oxide gas (EOG).

Features of the medical device holder 1 are described below. As shown in FIG. 1 to FIG. 4, the medical device holder 1 is formed of a flexible elongated sheet member 10. The medical device holder 1 is used in a state of being deformed (bending, curving) (bent state) such as by bending the sheet member 10 in the deployed state shown in FIG. 1 at predetermined portions as shown in FIG. 3 and FIG. 4.

The material of the sheet member 10 is not specifically limited, and may be various types of paper or paper-type products such as high-quality paper, middle-quality sheet, kraft paper, one-side glossy paper, rough kraft paper, cardboard, or surface coated paper, and one or a plurality of such paper materials are laminated (overlapped) for use.

The medical device holder 1 formed of the sheet member 10 as described above includes an elongated main body portion 11 on which the catheter 20 is placed, a holding portion 2 which holds the catheter body 201 and the hub 202 of the catheter 20, and a holding portion 3 provided at a position different and spaced from the holding portion 2 to hold the three-way stopcock 207.

The holding portion 2 is provided at a position slightly deviated to the upper side (one end portion) in FIGS. 1-3 in the direction of width (vertical direction in FIGS. 1-3) (direction vertical to the longitudinal direction) of the medical device holder 1 (sheet member 10).

The holding portion 2 includes eight tabs 4a, 4b, 4c, 4d, 4e, 4f, 4g and 4h. As shown in FIG. 1, the tabs 4a-4h are arranged at spaced apart intervals along the longitudinal direction (lateral direction in FIGS. 1-4) of the medical device holder 1 (sheet member 10). The tabs 4a-4h clamp or hold the catheter body 201 in cooperation with the main body portion 11 as shown in FIG. 3. Accordingly, the catheter body 201 is securely held by the holding portion 2.

The tabs 4a-4d from the tabs 4a-4h project downward in FIG. 1, and the tabs 4e-4h project upward in FIG. 1. The tabs 4a-4d and the tabs 4e-4h are arranged in an alternately manner from each other. In this configuration, even if the catheter body 201 of the catheter 20 held on the holding portion 2 is shifted (moved) downward in FIG. 3, the catheter body 201 is prevented from coming apart from (becoming separated from) the tabs 4a-4h.

Also, as shown in FIG. 3, the tab 4a and the tab 4e constitute one tab pair 40 which clamps the catheter body 201 intensively (intensively from point to point) on the holding portion 2. In the same manner, the tab 4b and the tab 4f constitute another tab pair 40, the tab 4c and the tab 4g constitute a further tab pair 40, and the tab 4d and the tab 4h constitute an additional tab pair 40. Accordingly, clamping forces for holding predetermined intermediate portions (midsections) of the catheter body 201 are increased, so that the catheter body 201 is fixed further reliably.

The respective tabs 4a-4h are formed by incising part of the sheet member 10 into an L-shape (V-shape or upside-down V-shape) or other desired bent shape. Accordingly, the respective tabs 4a-4h are formed relatively easily compared to forming the same separately. However, needless to say, the respective tabs 4a-4h may be formed separately.

The holding portion 2 includes an opening (hole) 21 formed on the proximal end side of the proximal-most pair of tabs 4a and 4e of the sheet member 10. As shown in FIG. 3, the opening 21 has an (elongated) rectangular shape and is a portion configured to allow insertion of the hub 202 of the catheter 20. Accordingly, the hub 202 of the catheter 20 is reliably held.

As shown in FIGS. 1-4, the holding portion 3 for holding the three-way stopcock 207 is positioned adjacent the holding portion 2 on the lower side (the other end side) of the holding portion 2 in FIGS. 1-3. In this arrangement, the catheter body 201 and the three-way stopcock 207 is held in a side-by-side arrangement, whereby the catheter 20 is retrieved smoothly.

As shown in FIG. 1 and FIG. 2, the holding portion 3 possesses an elongated rectangular shape before deformation (i.e., before being moved to hold/cover a part of the medical device), and the longitudinal direction of the holding portion matches the longitudinal direction of the sheet member 10 (catheter body 201). The holding portion 3 is located at an intermediate portion of the sheet member 10. More specifically, the holding portion 3 is positioned at midsections of the sheet member 10, that is at a midsection in the longitudinal direction of the sheet member 10 and a midsection in the direction vertical to the longitudinal direction.

As shown in FIG. 3 and FIG. 4, the holding portion 3 is deformed (curved, bent, etc.) along the longitudinal direction of the sheet member 10 (catheter body 201) so as to cover the three-way stopcock 207 in a state in which the catheter 20 is located on the main body portion 11. Accordingly, the three-way stopcock 207 is held reliably by the holding portion 3.

The three-way stopcock 207 is placed on the holding portion 3. The holding portion 3 is then moved in the proximal direction (i.e., to the left in FIG. 2) to bring the holding portion 3 in covering relation to the three-way stopcock 207 as shown in FIG. 4. In this way, a portion of the holding portion 3 is bent back upon itself so that, as illustrated in FIG. 4, a portion of the holding portion 3 underlies the three-way stopcock 207 and a portion of the holding portion overlies the three-way stopcock 207. In addition, the distal end of the three-way stopcock 207 faces toward the distal end of the sheet member 10 (i.e., the right end in FIGS. 1-4) while the proximal end of the three-way stopcock 207 faces toward the proximal end of the sheet member 10 (i.e., the left end in FIGS. 1-4). Once the holding portion 3 is moved in the proximal direction to overlie or cover the three-way stopcock 207, the entire portion of the three-way stopcock 207, except for lateral sides, is enveloped or covered by the holding portion 3. In other words, the entire three-way stopcock 207 is enveloped along the longitudinal direction of the sheet member 10 (catheter body 201). Accordingly, wall portions (sheet member) on a front side and a back side of the packaging member 30 are prevented from becoming damaged (broken) by the three-way stopcock 207, whereby the catheter 20 is adequately held and the catheter 20 can be transported and stored in an adequate state. In addition, when a plurality of the catheter sets 100 are stored in a box (storage container), the three-way stopcock 207 is prevented from catching other three-way stopcock 207 or certain members of the adjacent catheter sets 100 by the holding portion 3 when retrieving a certain catheter set 100 from the box, so that an operation to retrieve the same is achieved relatively easily and quickly.

As shown in FIG. 1 and FIG. 2, the proximal end side of the holding portion 3 includes a slit 5. The slit 5 operates as an receiving portion which receives and allows insertion of a distal end portion 31 of the holding portion 3 to hold the three-way stopcock 207 by the holding portion 3 in a covered state (held state). The slit 5 is formed by incising part of the sheet member 10 linearly (desired shape) in the widthwise direction of the sheet member 10. The slit 5 allows the holding portion 3 to maintain the three-way stopcock 207 in a covered state. Thus, the holding portion 3 is folded in the proximal direction (i.e., to the left in FIG. 2) to cover the three-way stopcock 207, and then the distal end portion 31 of the holding portion is inserted into the slit 5 and is folded back in the distal direction (i.e., to the right in FIGS. 3 and 4) as shown in FIG. 4.

The catheter 20 held on the medical device holder 1 is retrieved or removed from the medical device holder 1 by gripping the hub 202 and pulling the catheter 20 toward the proximal direction (i.e., toward the left in FIG. 4).

As shown in FIG. 3 and FIG. 4, the distal end portion 31 of the holding portion 3 is inserted into the slit 5 in a state in which the holding portion 3 covers the three-way stopcock 207, and is folded back toward the opposite side from the direction to pulling out the catheter 20 when removing from the holder 1. That is, as shown in FIG. 4, the distal end portion 31 of the holding portion is bent back toward the right (distal end side), whereas the force applied to the catheter 20 to remove or separate the catheter 20 from the holder 1 is to the left (proximal direction). Accordingly, when retrieving the catheter 20 from the medical device holder 1 of the catheter set 100, the distal end portion 31 of the holding portion 3 is prevented from being caught by the packaging member 30, whereby the distal end portion 31 of the holding portion 3 is smoothly and reliably pulled out from the slit 5, and hence the retrieving operation is achieved relatively easily and quickly.

In addition, although insertion of the holder 1 in the holding state into the packaging member 30 is achieved by pushing the medical device holder 1 inward in the direction toward the proximal end from the distal end portion of the packaging member 30, since the distal end portion 31 of the holding portion 3 is folded back toward the distal end side (the opposite side from the direction to push inward), the distal end portion 31 of the holding portion 3 is prevented from being caught by the packaging member 30 when inserting the holder 1 in the holding state into the packaging member 30, so that the inserting operation is achieved relatively easily and quickly.

As shown in FIG. 2, the width (the vertical length in FIG. 2) of the distal end portion 31 of the holding portion 3 is gradually increased from the distal end side toward the proximal end side. Alternatively, though not gradually increased from the distal end side toward the proximal end side, the width of the distal end portion 31 of the holding portion 3 is smaller at the distal end side of the distal end portion 31 than that of the proximal end side thereof. Accordingly, the distal end portion 31 of the holding portion 3 is inserted into the slit 5 relatively easily and smoothly.

As shown in FIG. 2 and FIG. 3, the distal end portion 31 of the holding portion 3 is provided with a hole (elongated hole or slit) 32 which allows insertion or accommodation of the tube 206 and is opened at the distal end of the distal end portion 31. Accordingly, a path for the tube 206 is provided and parts of the distal end portion of the holding portion on either side of the hole 32 straddle the tube 206 as generally illustrated in FIGS. 3 and 4. The hole 32 may be an opening formed by cutting out completely, but part of it may be remained in a state of being connected to the medical device holder 1 and, in this case, labor to dispose of the paper tip generated by forming the hole 32 on the medical device holder 1 is avoided.

As shown in FIG. 2 and FIG. 4, the holding portion 3 has two wall portions 33. The wall portions 33 are provided upright at both edge portions of the holding portion 3 in the widthwise direction (vertical direction in FIG. 2). The wall portions 33, which are delimited by the noted (dotted) folding lines or crease lines, are formed by inwardly folding towards one another (in the widthwise direction) longitudinally extending edge portions of the holding portion 3. By the formation of the respective wall portions 33, the holding portion 3 is reinforced. In addition, the three-way stopcock 207 is held further reliably by the holding portion 3 (i.e., the wall portions 33 help prevent the three-way stopcock from coming off from the holding portion 3).

The wall portions 33 are provided at the both edge portions of the holding portion 3 in the widthwise direction in the illustrated embodiment. However, the disclosure here is not limited to that configuration, an, may be provided at one of the edge portions for example.

As shown in FIG. 2, the holding portion 3 is formed by incising part of the sheet member 10 in an elongated rectangular shape (desired shapes). Accordingly, formation of the holding portion 3 is achieved more easily than the case of forming the same separately. There is also an advantage such that the manufacturing cost is lower than the configuration in which the holding portion 3 is formed separately. Also, since the holding portion 3 and the main body portion 11 are integrated, the holder 1 is advantageously easy to handle. However, needless to say, the holding portion 3 may be formed separately.

Preferably, the medical device holder 1 is provided (coated) with a resin layer of a resin material on the front surface (the surface on the side on which the catheter 20 is to be placed). Although the material of the resin layer is not specifically limited, for example, fluorinated resin such as PTFE (polytetrafluoroethylene), polyolefin such as polyamide, polyimide, polyethylene or polypropylene, polyester such as polyethylene terephthalate or polybutylene terephthalate, polyurethane, polystyrene, polycarbonate, silicone resin, polyetherimide are exemplified and, in these materials, low friction materials such as fluorinated resin or polyolefin are preferred.

With the formation of the resin layer, when the catheter 20 is pulled out from the medical device holder 1 in the direction toward the proximal end, the frictional resistance (sliding resistance) is reduced, so that the retrieving operation is relatively smoothly achieved. As an alternative to the resin layer on the front surface of the medical device holder 1, the low frictional surface can be achieved by providing minute projections and depressions on the front surface of the holder 1.

The resin layer may be formed respectively on the front surface and the back surface of the medical device holder 1. Also, the resin layer may be formed neither on the front surface nor the back surface of the medical device holder 1.

A thickness t of the holder 1 (sheet member 10) is preferably from 0.20 to 0.55 mm, and more preferably, from 0.3 to 0.5 mm. Accordingly, respective tabs 7a to 7f have an adequate clamping force (holding force) with respect to a second catheter 20b.

Retrieving the catheter 20 held on the holder 1 of the catheter set 100 from the holder 1 is achieved, for example, by separating (opening) the proximal end portion of the packaging member 30 to form an opening, holding the medical device holder 1, and pulling out (retrieving) the medical device holder 1 from the package opening in the direction toward the proximal end.

Subsequently, the user can hold the hub 202 of the catheter 20 and pull the catheter 20 in the direction toward the proximal end (i.e., toward the left in FIG. 4). This direction of the pulling force applied to the catheter 20 is opposite the direction in which the distal end portion 31 of the holding portion 3 is folded back (i.e., as shown in FIG. 4, the distal end portion 31 of the holding portion 3 is folded toward the distal direction (toward the right in FIG. 4). In this case, the three-way stopcock 207 is pulled in the direction toward the proximal end via the tube 206, whereby the distal end portion 31 of the holding portion 3 comes out (is pulled out) from the slit 5, and the three-way stopcock 207 is moved in the proximal end direction. In this manner, the catheter 20 is removed or separated from the holder 1.

As described above, since the distal end portion 31 of the holding portion 3 is folded toward the distal end side (the opposite side from the direction in which the holder and medical device are pulled out of the package and the opposite side from the direction in which the catheter is pulled out from the medical device holder 1) on the back surface of the medical device holder 1, when the three-way stopcock 207 is pulled in the proximal direction, the distal end portion 31 of the holding portion 3 is prevented from being caught on the packaging member 30 due to the three-way stopcock 207 when the distal end portion 31 of the holding portion 3 comes out from the slit 5, whereby the distal end portion 31 of the holding portion 3 comes out from the slit 5 rather smoothly and reliably, and hence the retrieving operation is achieved relatively easily and quickly.

The configuration of the distal end portion 31 of the holding portion 3 in the first embodiment may be applied to the holding portion in a second embodiment described later.

Here, the catheter set (medical device set) 100 may have a pocket (storage portion) 50 provided on the packaging member 30 as shown in FIG. 12A. In the following description, the right sides of FIG. 12A and FIG. 12B are referred to as the "distal end" and the left sides are referred to as the "proximal end".

Although the position of the pocket 50 is not specifically limited, the pocket 50 is illustrated as being provided at the distal end portion of the packaging member 30 in the configuration shown in the drawings. An opening 501 which functions as an insertion and output port is formed on the proximal end side of the pocket 50. A plurality of the pockets 50 may also be provided.

Accordingly, for example, predetermined accessories such as a surgical knife or a needle are conveniently stored in the pockets 50 in a state of being stored in a predetermined storage bag 90.

The catheter set (medical device set) 100 may have a belt member (holding portion) 60 which is capable of holding the storage bag 90 in which the accessories are stored as shown in FIG. 12B. The belt member 60 is wound around the outer periphery of the packaging member 30 along the circumferential direction, and is formed into an annular shape. As a detailed example of the belt member 60, for example, a piece of paper used as a wrapper is exemplified.

Although the position of the belt member 60 is not specifically limited, the belt member 60 is provided at a center portion of the packaging member 30 in the longitudinal direction in the configuration shown in the drawings. The belt member 60 may be fixed to the packaging member 30 with a fictional resistance, or may be secured partly to the packaging member 30 by fusion bonding or adhesive bonding. A plurality of the belt members 60 may be provided.

Figure 7:
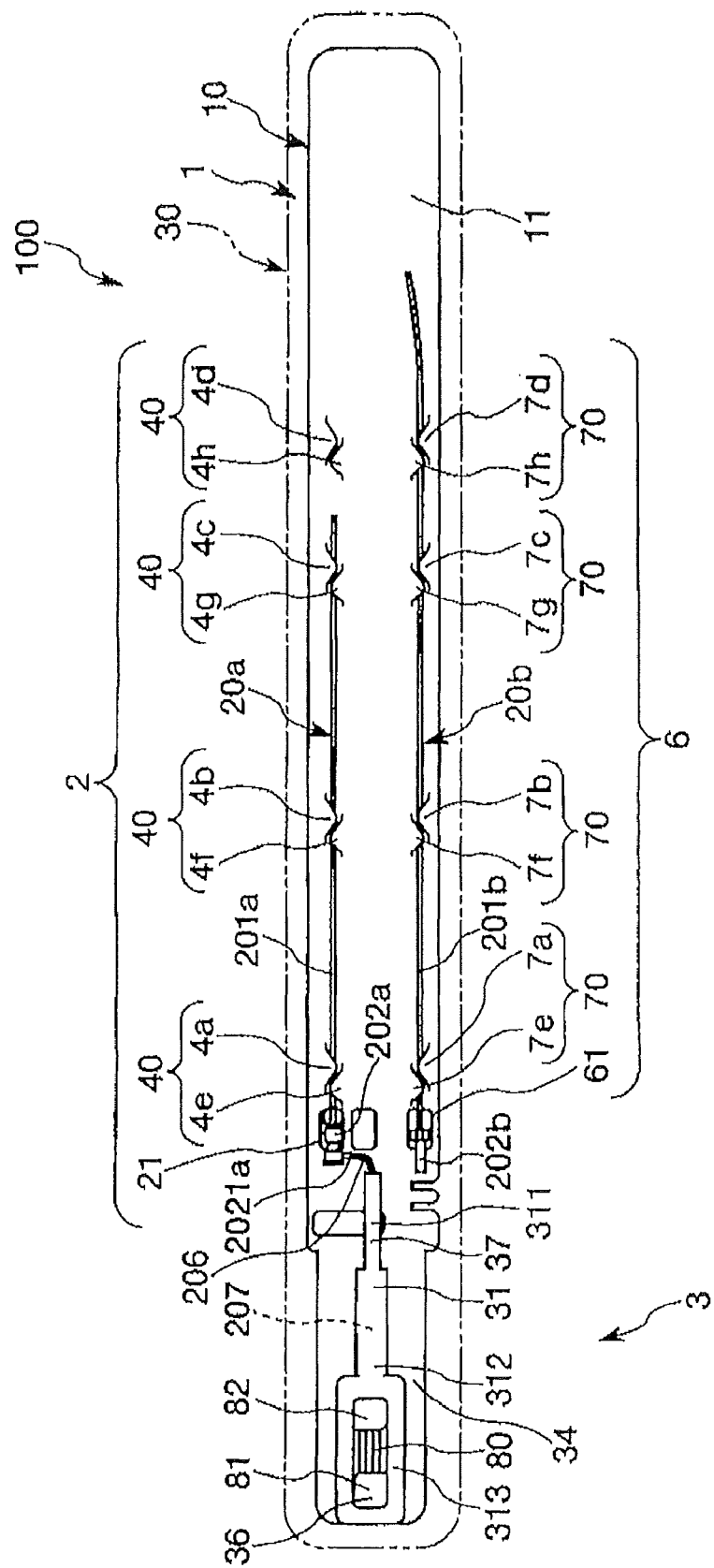
FIG. 7 is a plan view of the medical device holder shown in FIG. 5 in a state of usage.
Figure 8:
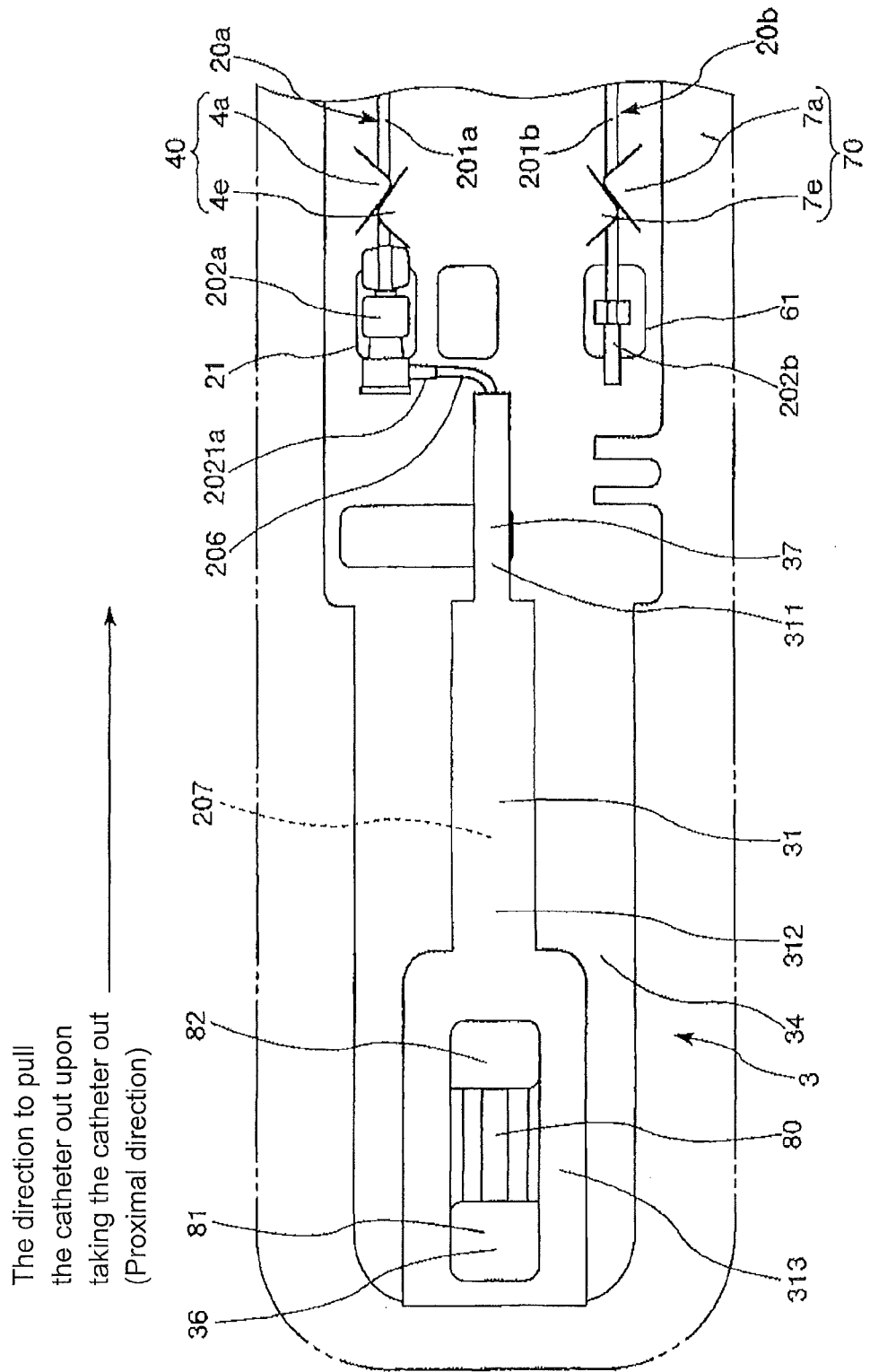
FIG. 8 is a plan view of the medical device holder shown in FIG. 5 showing a portion in the vicinity of the holding portion in the state of usage.
Figure 9:
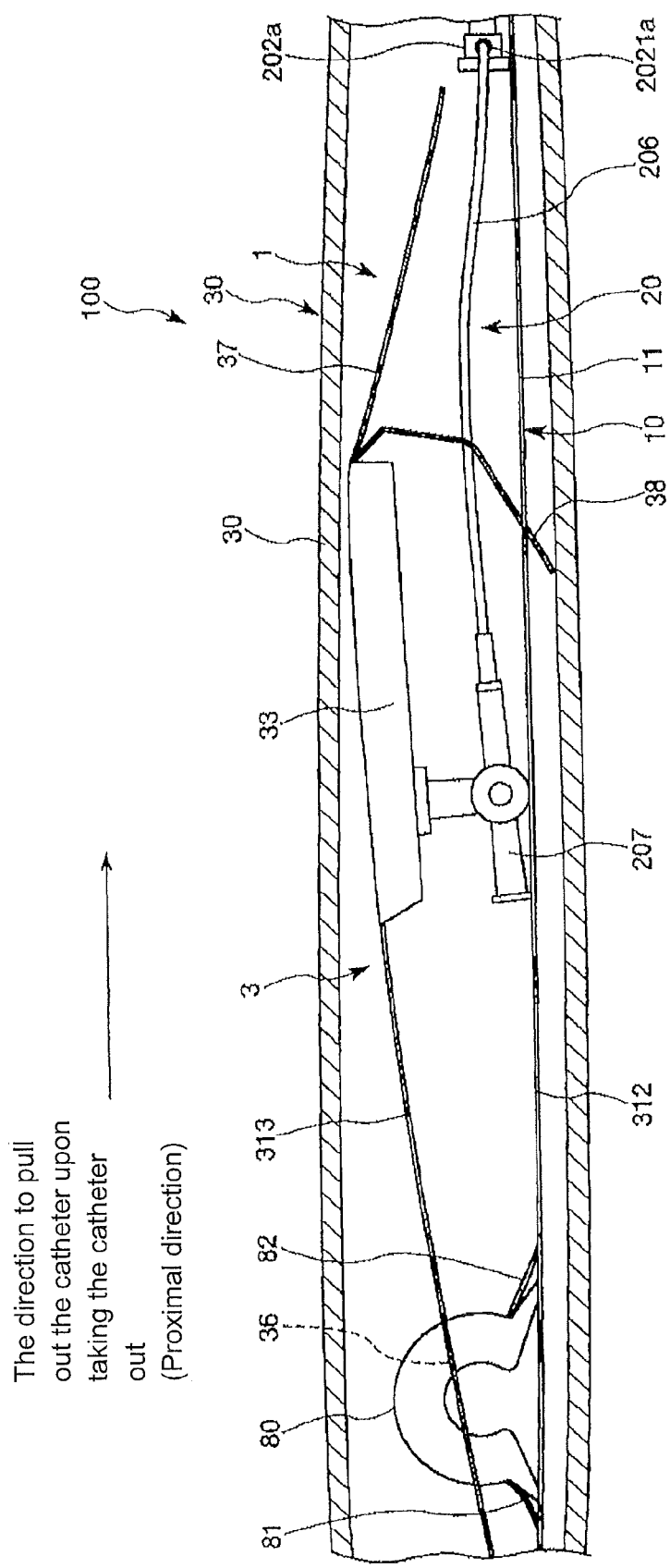
FIG. 9 is a side view of the medical device holder shown in FIG. 5 showing a portion in the vicinity of the holding portion in the state of usage.

FIGS. 5-9 illustrate aspects of a medical device holder according to a second embodiment disclosed here. In the following description, the right side of FIGS. 5-9 is referred to as the "distal end", and the left side is referred to as the "proximal end". The near (front) sides of the sheets of FIGS. 5-8 are referred to as the "front" and the far (back) sides of the sheets are referred to as then "back", and the upper side in FIG. 9 is referred to as the "front" while the lower side is referred to as the "back".

Figure 5:
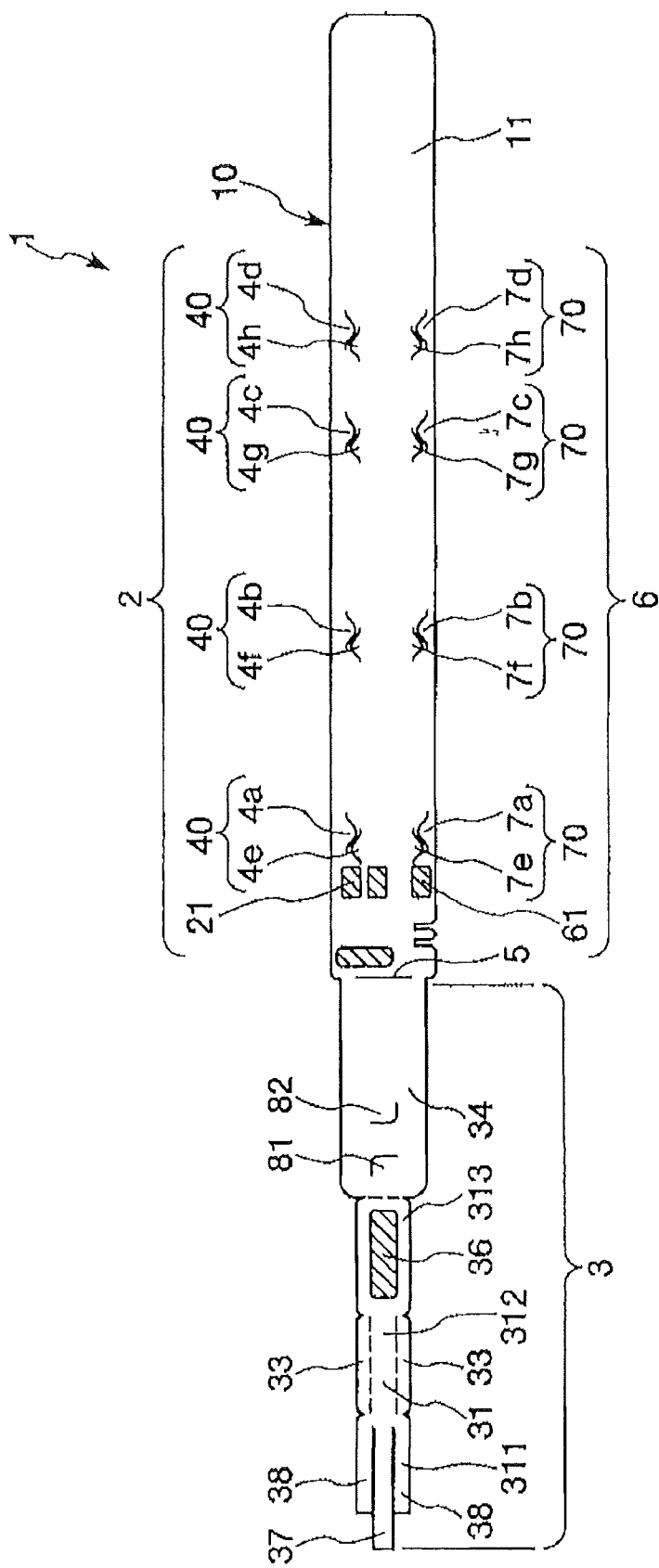
FIG. 5 is a plan view of a medical device holder according to a second embodiment disclosed here.
Figure 6:
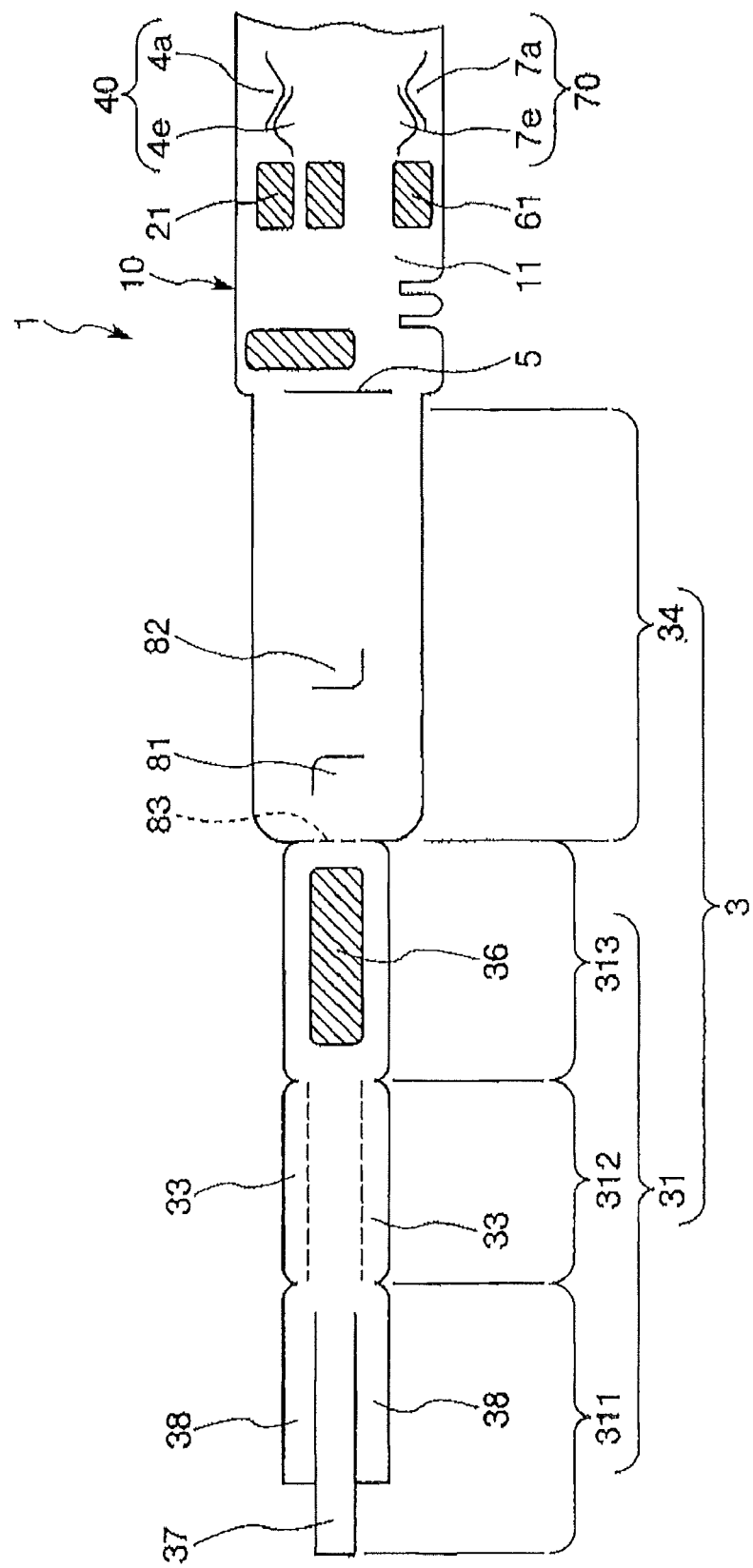
FIG. 6 is a plan view of the medical device holder shown in FIG. 5 in the vicinity of the holding portion.

Broken lines in FIG. 6 indicate valley folding portions and solid lines indicate incised portions. Hatched portions in FIG. 5 and FIG. 6 indicate through holes (openings).

The description which follows primarily describes features of the second embodiment of the medical device holder and medical device retrieving method that differ relative to features described above in the first embodiment. Features in this second embodiment that are the same as those in the first embodiment are identified by common reference numerals and a detailed discussion of such features will not be repeated.

In this disclosed embodiment, the medical device holder is a sheet-made or sheet-shaped medical device holder (hereinafter referred to simply as a holder or a medical device holder) 1 shown in FIGS. 5-9 is able to hold a plurality (two in the illustrated embodiment) of catheters (medical devices) 20a and 20b in unused condition.

The catheters 20a and 20b constitute a catheter assembly used in a state of being assembled (assembled state), that is in a state in which the catheter 20b is inserted into the catheter 20a.

The catheter 20a is the same as the catheter 20 in the first embodiment, and includes a flexible catheter body (linear portion) (elongated portion) 201a, a hub 202a on a proximal end portion of the catheter body 201a and having a port portion 2021a, the flexible tube (linear portion) 206 connected to a proximal end side of the catheter body 201a, that is to the port portion 2021a of the hub 202a, and the three-way stopcock (connecting member) (three-dimensional structure) 207 provided on the distal end portion of the tube 206.

The catheter body 201a has an inner diameter which is substantially the same as or larger than an outer diameter of a catheter body 201b of the catheter 20b, described later. Accordingly, when forming the assembled state (catheter assembly), it is possible to insert the catheter body 201b into the catheter body 201a.

The catheter 20b includes the flexible catheter body (linear portion) (elongated portion) 201b and a hub 202b provided at a proximal end portion of the catheter body 201b.

The catheter body 201b is formed of an elongated tube (hollow tube).

The hub 202b formed of the hard resin material is fixed (connected) to the proximal end portion of the catheter body 201b. The hub 202b is a cylindrical member having an outer diameter and an inner diameter larger than the outer diameter and inner diameter respectively of the catheter body 201b, and a bore of the hub is communicated with a bore of the catheter body 201b.

The material of the catheter body 201b is not limited in any particular manner, and the same material as of the catheter 20 in the first embodiment may be employed. The rigidities of the catheter body 201a and the catheter body 201b are differentiated by selecting the material of the catheter body 201a and the material of the catheter body 201b as needed, for example.

As shown in FIGS. 5-9, the medical device holder 1 includes the elongated main body portion 11 on which the catheters 20a, 20b are placed, the holding portion 2 for holding the catheter body 201a and the hub 202a of the catheter 20a, the holding portion 3 provided at a position different and spaced from the holding portion 2 for holding the three-way stopcock 207, and a holding portion 6 at a position different from the holding portion 2 and the holding portion 3 to hold the catheter body 201b and the hub 202b of the catheter 20b.

The configuration of the holding portion 2 is the same as the holding portion 2 in the first embodiment, and so a detailed description of the holding portion will not be repeated.

The holding portion 6 is provided on the lower side of the holding portion 2 in FIGS. 5-7 adjacent to the holding portion 2. In such a layout, the catheter 20a and the catheter 20b are held in a side-by-side arrangement, whereby the retrieving operation of the respective catheters is achieved relatively easily.

The holding portion 6 includes the eight tabs 7a, 7b, 7c, 7d, 7e, 7f, 7g and 7h. The tabs 7a-7d from among the tab 7a-7h project upward in FIG. 5, and the tabs 7e-7h project downward in FIG. 5. The tab 7a and the tab 7e constitute one tab pair 70, the tab 7b and the tab 7f constitute another tab pair 70, the tab 7c and the tab 7g constitute an additional tab pair 70, and the tab 7d and the tab 7h constitute a further tab pair 70.

The holding portion 6 includes an opening (hole) 61 formed on the proximal end side of the tabs 7a and 7e of the sheet member 10. As shown in FIG. 7, the opening 61 has an (elongated) rectangular shape and is a portion that receives, and in which is inserted, the hub 202b of the catheter 20b. Accordingly, the hub 202b of the catheter 20b is reliably held.

As shown in FIGS. 5-9, the holding portion 3 for holding the three-way stopcock 207 is on the proximal end side of the slit 5, that is on the proximal end portion of the sheet member 10 in the longitudinal direction. In this arrangement, the catheter 20a is relatively smoothly retrieved. As regards the holding portion 3, the right sides of FIG. 5 and FIG. 6 are referred to as the "distal end" and the left sides are referred to as the "proximal end".

Two tabs 81 and 82 are formed on the distal end side (left sides in FIG. 5 and FIG. 6) of a proximal end portion 34 of the holding portion 3. The tab 81 projects rightward and upward in FIG. 5 and FIG. 6, and the tab 82 projects leftward and downward in FIG. 5 and FIG. 6. As shown in FIGS. 7-9, a fixing member 80 is clamped between the respective tabs 81 and 82 and the proximal end portion 34 of the holding portion 3. Accordingly, the fixing member 80 is held reliably.

The fixing member 80 is a member for fixing the catheter 20a and the catheter 20b with respect to each other when the assembled state (catheter assembly) is achieved. Since the fixing member 80 is rounded, the packaging member 30 is prevented from becoming damaged by the fixing member 80 even though the fixing member 80 is not covered with the holding portion 3.

The distal end portion 31 of the holding portion 3 includes a first region 311, a second region 312, and a third region 313 from the distal end side toward the proximal end side in sequence along the longitudinal direction of the sheet member 10.

The third region 313 has an opening (hole) 36. As shown in FIGS. 7-9, the opening 36 has a (elongated) square shape, and the fixing member 80 being held is positioned in the opening 36 in a state in which the holding portion 3 covers (holds) the three-way stopcock 207. Accordingly, the third region 313 is prevented from being excessively bulky by the fixing member 80 in the state in which the holding portion 3 covers the three-way stopcock 207.

The second region 312 has the two wall portions 33 as in the first embodiment.

The first region 311 includes inserting portions 38 to be inserted into the slit 5 respectively on both sides in the widthwise direction of the holding portion 3, and includes a center portion 37 which is not inserted into the slit 5 between the two inserting portions 38. The center portion 37 and the respective inserting portions 38 have a (elongated) square shape, respectively. The lengths of the respective inserting portions 38 in the longitudinal direction are the same. Then, the length of the center portion 37 in the longitudinal direction is set to be longer than the respective inserting portions 38 and a distal end portion of the center portion 37 projects toward the distal end side with respect to distal end portions of the respective inserting portions 38. The length of the center portion 37 in the longitudinal direction may be shorter than the length of the respective inserting portions 38 in the longitudinal direction. The center portion 37 and/or the respective inserting portions 38 may have a width tapered from the proximal end side toward the distal end side, and the distal end sides thereof may be rounded.

The procedure for holding the three-way stopcock 207 by the holding portion 3 is as follows. As shown in FIGS. 7-9, when holding the three-way stopcock 207 by the holding portion 3, the three-way stopcock 207 is arranged on the front surface side of the proximal end portion 34 of the holding portion 3.

Subsequently, the distal end portion 31 is folded at a valley fold portion 83 (see FIG. 6) with respect to the proximal end portion 34, and the respective inserting portions 38 of the first region 311 of the distal end portion 31 are folded at predetermined portions and are inserted into the slit 5.

Here, the catheter 20*a* held on the holder 1 is retrieved from the holder 1 by holding a distal end portion of the catheter body 201*a* and pulling the catheter 20*a* out in the direction toward the distal end (right side in FIGS. 7-9).

Therefore, the respective inserting portions 38 are folded back in a direction opposite the direction of the force applied when pulling out the catheter to remove the catheter 20 from the medical device holder 1. That is, the respective inserting portions 38 are folded back toward the proximal end side (left side in FIG. 9).

In contrast, the center portion 37 is not inserted into the slit 5, and is arranged on the front surface side of the main body portion 11 on the distal end side of the slit 5.

In this manner, the three-way stopcock 207 is enveloped (covered) entirely except for the lateral sides by the holding portion 3. In other words, the entire portion of the three-way stopcock 207 is enveloped along the longitudinal direction of the sheet member 10 (catheter body 201*a*) by the holding portion 3.

Retrieving the catheter 20*a* held on the medical device holder 1 of the catheter set 100 from the medical device holder 1 is achieved by, for example, separating the proximal end portion of the packaging member 30 to form an opening, holding the holder 1, and pulling out a portion of the holder 1 including the holding portion 3 from the opening in the direction toward the proximal end.

Then, the hub 202*a* of the catheter 20*a* is held and the catheter body 201*a* of the catheter 20*a* is pulled out. In this case, the hub 202*a* is pulled upward so that the three-way stopcock 207 is pulled in the direction toward the distal end via the tube 206, whereby the respective inserting portions 38 of the distal end portion 31 of the holding portion 3 come out from the slit 5, and the three-way stopcock 207 is moved in the direction toward the distal end. In this manner, the catheter 20*a* is retrieved from the medical device holder 1.

According to this embodiment, results and advantages similar to those described in the first embodiment can be realized.

The configuration of the distal end portion of the holding portion in the second embodiment may be applied to the holding portions in the first embodiment described above and a third embodiment described below.

Figure 10:
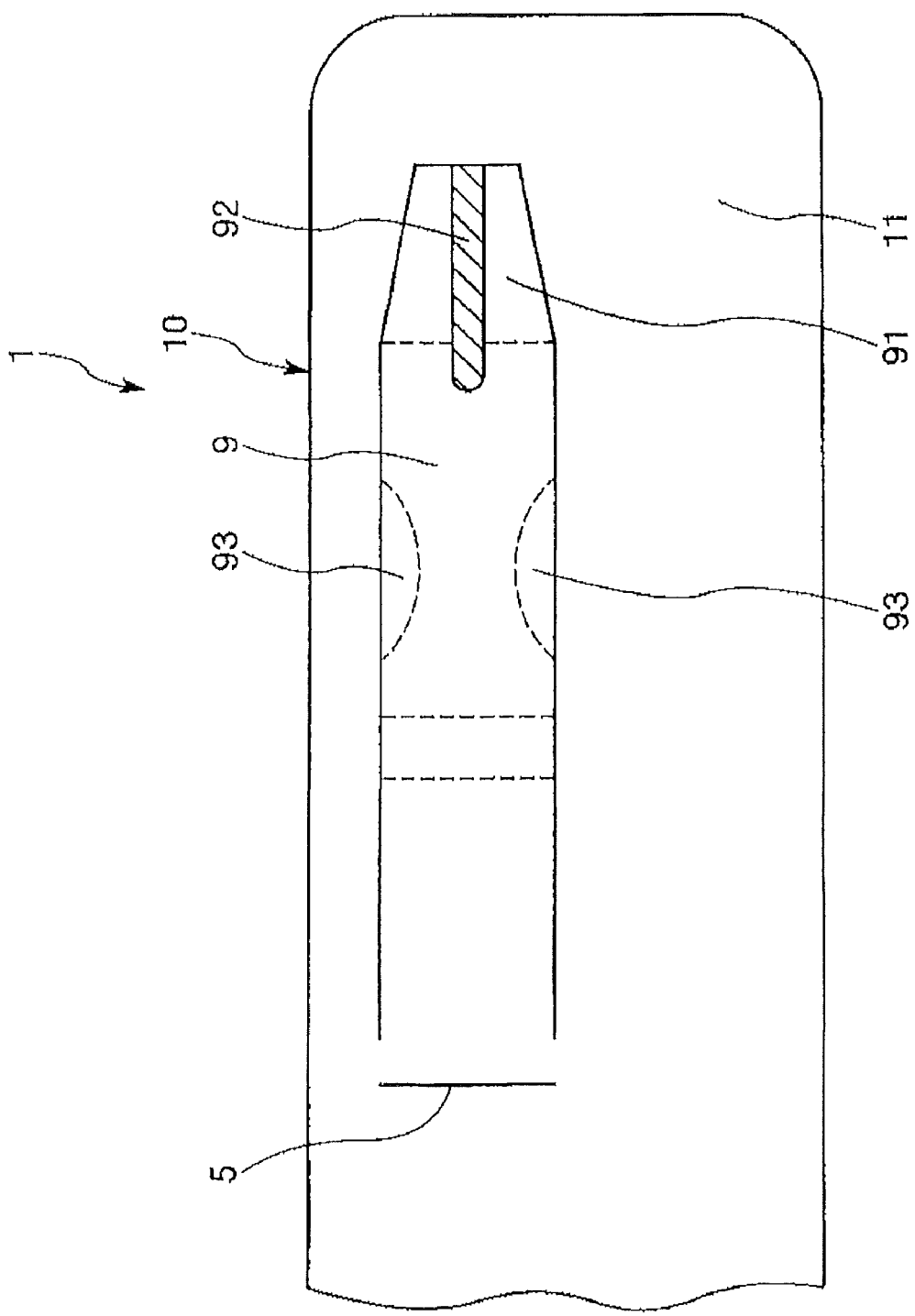
FIG. 10 is a plan view of a principal portion of a medical device holder according to a third embodiment disclosed here.

FIGS. 10 and 11 illustrate principal portions of the medical device holder according to a third embodiment disclosed here, and aspects of usage.

In the following description, the right sides in FIGS. 10 and 11 are referred to as the "distal end" and the left sides are referred to as the "proximal end". The near (front) sides of the sheets in FIGS. 10 and 11 are referred to as the "front", and the far (back) sides of the sheets are referred to as "back".

Broken lines in FIG. 10 indicate portions to be valley folding portions and solid lines indicate incised portions, and the hatched portion indicates a through hole (opening).

The description which follows primarily describes features of the third embodiment of the medical device holder and medical device retrieving method that differ relative to features described above in the first embodiment. Features in this second embodiment that are the same as those in the embodiments described above are identified by common reference numerals and a detailed discussion of such features will not be repeated.

This embodiment of the medical device holder is a sheet-made or sheet-shaped medical device holder. In the third embodiment, a distal end portion 203 of the catheter body 201 of the catheter 20 held by the sheet-shaped medical device holder (hereinafter referred to simply as a holder or medical device holder) is curved into a desired shape (deformed into a curved shape) in a state in which an external force is not applied. In the configuration shown in the drawings, the distal end portion (deformed portion) 203 is curved into a helical shape (the shape of a plurality of loops) in the state in which the external force is not applied, whereby a helical portion (a three-dimensional structure) is formed.

The distal end portion 203 is not limited to the illustrated curved configuration, but may be formed with as a structure that is bent (deformed into a bent shape) into a three-dimensional form, or may be formed with a structure that is curved and bent into a three-dimensional structure.

As shown in FIGS. 10 and 11, the medical device holder 1 is provided with a holding portion 9 for holding the distal end portion 203 of the catheter body 201 of the catheter 20 in addition to the components in the first embodiment. The holding portion 9 is arranged on the distal end side of the holding portion 2.

The configuration of the holding portion 9 is the same as the holding portion 3 in the first embodiment. In other words, the holding portion 9 has two wall portions 93 and a distal end portion 91 of the holding portion 9 is formed with a hole or slit 92 which allows insertion of the tube 206 and is opened at the distal end of the distal end portion 91.

According to the medical device holder 1, the same effects as the first embodiment as described above will be obtained.

With the medical device holder 1, the wall portions (sheet members) on the front side and the back side of the packaging member 30 are prevented from becoming damaged (broken) by the distal end portion 203 of the catheter body 201 by the holding portion 9.

The structure of the distal end portion 203 of the catheter body (linear portion) 201 is not limited to being configured of the catheter body 201, and may be configured separately. As a detailed description, for example, a removing member configured to hollow out and remove an occlusion which narrows or occludes a bore of a tubular organ such as vessels in an atherectomy catheter and, likewise, a removing member of an intravascular plaque foreign substance removing catheter, a sheath member of a continuous epidural anesthesia catheter, an electrode member of an electrode catheter, an abrasion member of an abrasion catheter, and an occlusion member of an occlusion catheter are examples.

The three-way stopcock (connecting member or three-dimensional structure) 207 or the tube (linear portion) 206 in the catheter (medical device) 20 may be omitted. In this case, the holding portion 3 for the three-way stopcock is omitted.

The two holding portions 3 and 9 may be replaced by the holding portion in the second embodiment, respectively, or one of the two holding portions described above may be replaced by the holding portion in the second embodiment.

A configuration of the distal end portion of the holding portion in the second embodiment may be applied to the two holding portions 3 and 9, respectively, or the configuration of the distal end portion in the first embodiment may be applied to one of the two holding portions 3 and 9 and the configuration of the distal end portion of the holding portion in the second embodiment may be applied to the other one of those.

The medical device holder, the medical device retrieving method, and the packaging member disclosed here are described on the basis of the embodiments shown in the drawings. However, the invention is not limited thereto, and the respective members which constitute the medical device holder may be replaced by ones having an arbitrary configuration different from that shown but which nevertheless demonstrates the same or similar functions. Also, arbitrary structures or processes may be added.

The invention may be a combination of the arbitrary two or more configurations (characteristics) in the respective embodiments described above.

In the embodiments described above, one or two holding portions which hold the structure having a three-dimensional structure are provided. However, three or more of the holding portions may be provided in the invention.

The medical device held on the medical device holder in the invention is not limited to the catheter described in the embodiments described above, and may be the one having the solid linear portion, for example. As other detailed examples of the catheter, for example, a guide wire, a sheath, and a dilator are exemplified.

The detailed description above describes preferred embodiments of the medical device holder, the medical device retrieving method, and the packaging member. However it is to be understood that the invention is not limited to those precise embodiments described and illustrated above. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A packaged medical device comprising:
a medical device comprising a flexible linear portion and a three-dimensionally configured part, the distal end portion of the flexible linear portion being connected to the three-dimensionally configured part, the three-dimensionally configured part being enlarged relative to the distal end portion of the flexible linear portion;
an elongated sheet member on which the medical device is held, the sheet member possessing a proximal end and a distal end, the sheet member comprising a slit passing through the sheet member and a holding portion possessing a distal end portion, a first part of the holding portion underlying the three-dimensionally configured part and a second part of the holding portion overlying the three-dimensionally configured part so that the three-dimensionally configured part is covered by the holding portion;
the distal end portion of the holding portion extending through the slit in the sheet member and being folded back toward the distal end of the sheet member in a direction opposite a direction in which the medical device is pulled to remove the medical device from the holder; and
the sheet member and the medical device held on the sheet member being sealed within a package.

2. The packaged medical device according to claim 1, wherein the three-dimensionally configured part is a three-way stopcock.

3. The packaged medical device according to claim 1, wherein the sheet member comprises a plurality of spaced apart tabs, each of which engages and holds part of the flexible linear portion.

4. The packaged medical device according to claim 1, wherein the distal end portion of the holding portion includes a slot, the flexible linear portion of the medical device passing through the slot so that parts of the distal end portion of the holding portion straddles the flexible linear portion of the medical device.

5. The packaged medical device according to claim 1, wherein the medical device is a first medical device, and further comprising a second medical device separate from the first medical device and comprising a flexible linear portion, the sheet member comprising a plurality of spaced apart holding tabs each engaging a part of the flexible linear portion of the second medical device to hold the second medical device in place on the sheet member.

6. The packaged medical device according to claim 1, wherein the medical device is a first catheter, and further comprising a second catheter separate from the first catheter and comprising a flexible linear portion, the sheet member comprising a plurality of spaced apart holding tabs each engaging a part of the flexible linear portion of the second catheter to hold the second catheter in place on the sheet member.

7. A medical device holder configured to hold a medical device provided with a three-dimensionally configured part at an end portion of a flexible linear portion, the medical device holder comprising:
an elongated sheet member for holding the medical device and to permit the medical device to be separated from the sheet member by applying a force to the medical device moving the medical device in a proximal direction relative to the sheet member, the sheet member being comprised of a holding portion and an insertion portion;
the holding portion being an elongated part of the sheet member outlined by an incision which separates the elongated part from a surrounding part of the sheet member to allow the holding portion to be moved relative to the surrounding part of the sheet member and be bent back upon itself to cover and hold the three-dimensionally configured part of the medical device;
the holding portion possessing a distal end portion;
the insertion portion of the holding portion comprising a slit passing completely through the sheet member for receiving the distal end portion of the holding portion after the holding portion is bent back upon itself in a longitudinal direction of the holding portion to cover the three-dimensionally configured part of the medical device;

the distal end portion of the holding portion being foldable back in a distal direction opposite the proximal direction after the distal portion is inserted into the slit; and the holding portion possessing foldable wall portions defined by fold lines or crease lines, the foldable wall portions being positioned along opposite longitudinal edges of the holding portion and being foldable inwardly towards each other in a widthwise direction.

8. The medical device holder according to claim 7, wherein the distal end portion of the holding portion comprises an elongated opening that opens to a distal end of the holding portion.

9. The medical device holder according to claim 7, wherein the distal end portion of the holding portion comprises an elongated opening that opens to a distal end of the holding portion.

10. The medical device holder according to claim 7, wherein the holding portion is located at a midsection of the sheet member.

11. The medical device holder according to claim 7, wherein the holding portion is provided at an endmost portion of the sheet member in the longitudinal direction.

12. The medical device holder according to claim 7, wherein the sheet member comprises a layer of resin material on at least one surface of the sheet member.

13. The medical device holder according to claim 7, wherein the sheet member possesses a thickness from 0.20 mm to 0.55 mm.

14. The medical device holder according to claim 7, wherein the holding portion has an elongated rectangular shape.

15. A method of retrieving a medical device from a medical device holder, the medical device holder comprising: a medical device, an elongated sheet member possessing a distal end, and packaging in which the medical device and the sheet member are sealed; the medical device comprising a flexible linear portion and a three-dimensionally configured part connected to a distal end portion of the flexible linear portion; the sheet member comprising a slit passing through the sheet member and a holding portion possessing a distal end portion, the three-dimensionally configured part being positioned on the sheet member with the holding portion covering the three-dimensionally configured part is covered; the distal end portion of the holding portion extending through the slit in the sheet member and being folded back in the distal direction toward the distal end of the sheet member; the method comprising:

opening the packaging to gain access to the sheet member and the medical device;

pulling the medical device in a proximal direction, opposite the direction in which the holding portion is folded back, to move the medical device relative to the sheet member and cause the three-dimensionally configured part to apply a force to the holding portion which pulls the distal end portion of the holding portion out of the slit so that the medical device is separable from the sheet member.

16. The method according to claim 15, further comprising at least partially removing the medical device and the sheet member from the packaging after opening the packaging but before pulling the medical device relative to the sheet member.

17. A packaged medical device comprising:

a medical device comprising a flexible linear portion and a three-dimensionally configured part, the distal end portion of the flexible linear portion being connected to the three-dimensionally configured part, the three-dimensionally configured part being enlarged three-dimensionally relative to the distal end portion of the flexible linear portion;

an elongated sheet member on which the medical device is held, the sheet member possessing a proximal end and a distal end positioned at opposite ends of the elongated sheet member in a lengthwise direction of the sheet member, the sheet member comprising a slit passing through the sheet member and a holding portion possessing a distal end portion, the slit extending linearly in a widthwise direction of the sheet member, a first part of the holding portion underlying the three-dimensionally configured part and a second part of the holding portion overlying the three-dimensionally configured part so that the three-dimensionally configured part is covered by the holding portion;

the distal end portion of the holding portion passing through the slit in the sheet member and being folded back toward the distal end of the sheet member in a direction opposite a direction in which the medical device is pulled to remove the medical device from the holder; and the sheet member and the medical device held on the sheet member being sealed within a package.

18. The packaged medical device according to claim 17, wherein the sheet member comprises a plurality of spaced apart tabs, each of which is positioned in overlying relation to the flexible linear portion and each of which engages and holds part of the flexible linear portion.

19. The packaged medical device according to claim 17, wherein the distal end portion of the holding portion includes a slot which opens to a distal-most end of the holding portion, the flexible linear portion of the medical device passing through the slot so that parts of the distal end portion of the holding portion straddle the flexible linear portion of the medical device.

* * * * *